United States Patent [19]

Luberoff et al.

[11] 4,006,194

[45] Feb. 1, 1977

[54] PRODUCTION OF PHENOLS

[75] Inventors: Benjamin J. Luberoff, Summit; Todd S. Simmons, Montclair, both of N.J.

[73] Assignee: The Lummus Company, Bloomfield, N.J.

[22] Filed: May 17, 1971

[21] Appl. No.: 143,845

[52] U.S. Cl. .................. 260/621 C; 260/593 A; 260/601 R; 260/606; 260/610 R; 260/632 R; 260/624 R; 260/626 T

[51] Int. Cl.$^2$ .................................. C07C 37/00

[58] Field of Search ........ 260/621 C, 610 R, 632 R

[56] References Cited

UNITED STATES PATENTS

| | | | |
|---|---|---|---|
| 2,628,983 | 2/1953 | Allen et al. | 260/621 C |
| 2,883,430 | 4/1959 | De Jorg | 260/621 C |
| 2,906,789 | 9/1959 | McNaughtan | 260/621 C |
| 3,365,375 | 1/1968 | Nixon | 260/621 C |

*Primary Examiner*—Norman Morgenstern
*Attorney, Agent, or Firm*—Marn & Jangarathis

[57] ABSTRACT

Phenols are produced from $\alpha$-aralkyl peroxides, preferably alkyl- $\alpha$ -phenalkyl peroxides or diphenalkyl peroxides, by heating the peroxide in the presence of an acid catalyst and continuously separating volatile reaction products other than the phenol; i.e., a carbonyl compound and alcohol if formed, from the reaction mixture, preferably by bubbling a stripping gas therethrough. Phenol may be produced from an alkyl benzene by reacting the alkyl benzene with t-butyl hydroperoxide to produce a t-butyl- $\alpha$ -phenalkyl peroxide which is then decomposed in the presence of an acid catalyst. The reaction co-products include t-butanol and a carbonyl compound corresponding to the alkyl group.

7 Claims, 1 Drawing Figure

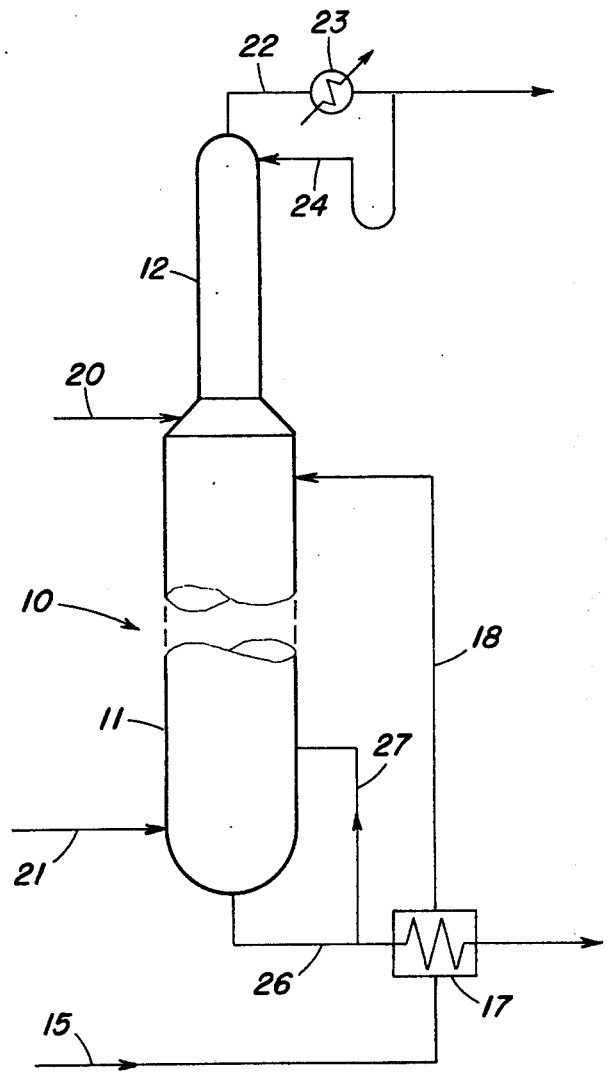
INVENTORS
Benjamin J. Luberoff
Todd S. Simmons
BY Marn & Jangarathis
ATTORNEYS

PRODUCTION OF PHENOLS

This invention relates to the production of phenols and more particularly to the production of phenols from α-aralkyl peroxides. This invention further relates to an overall process for producing phenols from an alkyl substituted aromatic compound and an alkyl hydroperoxide.

Phenol has been produced by the oxidation of cumene to cumyl hydroperoxide which is then decomposed in the presence of an acid catalyst to phenol and acetone. There is a continuing need for new processes for producing phenol in particular, processes which are capable of producing byproducts other than acetone and are also capable of producing phenol through a more stable intermediate.

Accordingly, an object of this invention is to provide a new process for producing phenols.

Another object of this invention is to provide a process for producing a phenol by the decomposition of an α-aralkyl peroxide.

A further object of this invention is to provide a process for producing phenols from an alkyl substituted aromatic compound and an alkyl hydroperoxide.

These and other objects of the invention should be more apparent from reading the following detailed description thereof with reference to the accompanying drawing, wherein:

The drawing is a simplified schematic diagram of a reactor to be used in an embodiment of the invention.

The objects of this invention are broadly accomplished in one aspect by decomposing an aromatic peroxide characterized by having as one or both of its moieties an α-aralkykl group, and if applicable as its other, an alkyl group, in the presence of a suitable catalyst and in a manner such that the volatile products of reaction; i.e., the carbonyl compound corresponding to the alkyl portion of the α-aralkyl moiety and alcohol, if formed, corresponding to the alkyl moiety, are continuously separated from the reaction environment; i.e., such reaction products are separated from the reaction mixture as formed.

In another aspect, the objects of the invention are accomplished by reacting an alkyl substituted aromatic compound with an alkyl hydroperoxide to produce an α-aralkyl peroxide which is then decomposed to phenol.

More particularly, the α-aralkyl alkyl peroxide, is decomposed at a temperature from about 20° to about 150° C., preferably from about 70° to about 110° C., in the presence of an acid catalyst, either a protonic acid or a Lewis acid, in a manner such that the volatile reaction products, (the carbonyl compound and alcohol, if formed) are continuously separated from the reaction mixture. The volatile reaction products a preferably separated from the reaction mixture by the use of a stripping gas which continuously strips the volatile products from the mixture. It is to be understood, however, that techniques other than the use of a stripping gas are within the spirit and scope of the invention e.g., distillation, although the use of a stripping gas is preferred. It is also to be understood that the material used as a stripping gas may also be a catalyst for the reaction; e.g., sulfur dioxide functions as both catalyst and stripping gas.

The material employed as the stripping gas may be comprised of any of a wide variety of materials which do not adversely affect the decomposition reaction, and as representative examples of such gases, there may be mentioned: The lower hydrocarbons, nitrogen, alkyl aromatic compounds (preferably the alkyl aromatic compound from which the peroxide is derived) and the like. The stripping gas may also be formed from a material which catalyzes the reaction; e.g., sulfur dioxide, in which case no additional catalyst need be added. The choice of a stripping gas for a particular decomposition reaction is deemed to be well within the scope of those skilled in the art from the teachings herein.

The decomposition reaction may be effected in the presence or absence of solvent as a batch or continuous process. The solvent, if employed, is preferably either an alkyl aromatic compound from which the peroxide is derived or a mixture of such an aromatic compound with the alcohol reaction product of the decomposition. It is to be understood, however, that any one of a wide variety of solvents which do not adversely affect the decomposition reaction are included within the spirit and scope of the invention.

The process of the invention is applicable to the decomposition of a wide variety of α-aralkyl peroxides with the term α-aralkyl peroxides as used herein denoting the class of compounds having as one or both of its moieties an aromatic nucleus substituted with an organic peroxymethyl group wherein the methylene group is unsubstituted or one or both of the hydrogens of the methyl group is substituted with an alkyl group and the aromatic nucleus may be free of substituent groups other than the alkyl peroxymethyl group or contain other substituent groups and if applicable as its other moiety an alkyl group; the following structural formula is representative of such compounds:

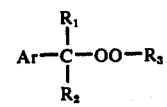

wherein $R_1$ and $R_2$ may be the same or different groups and are either hydrogen or alkyl (preferably lower alkyl); $R_3$ is alkyl (preferably lower alkyl, with tertiary lower alkyl being particularly preferred) or phen (lower) alkyl; and Ar is either a phenyl, naphthyl (α or β-naphthyl,) anthranyl (1,2 or 9 anthranyl), or phenanthranyl (1-, 2-, 3- or 9-phenanthranyl) radical, (preferably a phenyl radical) or substituted derivatives of such radicals wherein the substituent groups are either halo (preferably chloro-), lower alkyl, lower alkoxy, nitro or cyano. The term lower alkyl as used herein includes up to about six carbon atoms.

The preferred peroxides are the lower alkyl- α-phen (lower) alkyl peroxides and the di- α-phen (lower) alkyl peroxides and as representative examples of such preferred peroxides, there may be mentioned: t-butyl-α-phenethyl peroxide; t-butyl-α-tolyl peroxide; t-butyl-2-phenylisobutyl peroxide; t-butyl cumyl peroxide; di-α-phenethyl peroxide; dicumylperoxide; cumyl-α-phenethyl peroxide, and the like. It is to be understood that the hereinabove noted representative examples are only illustrative and, therefore, the scope of the invention is not to be limited thereby.

The catalyst which is employed may be any one of the wide variety of acid catalysts which are generally employed to decompose aromatic hydroperoxides; i.e., any material which provides an acidic pH in water, and as representative examples of such catalysts there may be mentioned: sulfuric acid, hydrochloric acid, benzene sulfonic acid, p-toluene sulfonic acid, phosphoric acid, trichloroacetic acid, stannic chloride, sulfur dioxide, zinc chloride, ferric chloride, aluminum chloride, boron trifluoride, hydrogen fluoride, perchloric acid and the like. The catalyst is generally employed in an amount ranging from about 0.01% to about 10%, and preferably in an amount ranging from about 0.1% to about 2%, all by weight, based on peroxide. It is to be understood, however, that other amounts of catalyst than those hereinabove noted may be employed although the stated amounts are preferred for economic reasons.

The peroxide decomposition is preferably effected in the presence of water in that the presence of water generally results in an increased yield. The water may be conveniently added to the system by employing steam as the stripping gas or by adding steam to the stripping gas. It is to be understood, however, that water may be introduced into the system in a manner other than with or as the stripping gas.

In accordance with a preferred procedure of the invention, the reaction is effected in a vertically disposed columnar reactor in which net flow is downward, with minimal back mixing, and the volatile reaction products are continuously withdrawn as overhead from the column and phenol reaction product is withdrawn as bottoms. The preferred procedure of the invention will be described with reference to the accompanying drawing which is a schematic representation of a reactor which may be used in the preferred procedure.

Referring now to the drawing, there is illustrated a vertically disposed columnar reactor 10 comprised of a lower reaction portion 11 and an upper fractionation portion 12, the fractionator portion containing suitable liquid-vapor contacting devices (not shown). The reaction portion 11 may also be provided with suitable vapor-liquid contacting devices or baffles to assist in separating volatile components from the reaction mixture. The reaction portion 11 preferably has a length to diameter ratio of at least about 10:1 in order to maximize the temperature gradient from the inlet to the outlet thereof and minimize back mixing therein.

A peroxide, such as t-butyl -α- phenethyl peroxide in line 15 is passed through a heat exchanger 17 to effect heating thereof by indirect heat transfer with reaction product, as hereinafter described. The preheated peroxide in line 18 is then introduced into the top of the reaction portion 11 of reactor 10.

A suitable catalyst, such as benzene sulfonic acid, dissolved or suspended in a reaction solvent, such as ethylbenzene, is introduced into the top of the reaction portion 11 of reactor 10 through line 20. The reaction mixture comprised of alkyl aromatic solvent, peroxide and catalyst is passed downwardly through the reaction portion 11 at a rate of flow to minimize back mixing and provide the required residence time. The reaction is exothermic and the heat of reaction vaporizes the volatile alcohol and carbonyl products of reaction.

A volatile liquid, such as iso-butane, is introduced into the bottom of the reaction portion 11 of reactor 10 through line 21 and under the conditions maintained in the reaction portion the liquid is immediately vaporized, thereby providing a stripping gas to facilitate removal of the alcohol and carbonyl reaction products from the reaction mixture.

The stripping gas, including vaporized alcohol and carbonyl reaction products, enters the fractionation portion 12 of reactor 10 and as a result of the fractionation therein, an overhead relatively free of reactants and phenol reaction product is withdrawn through line 22. The overhead in line 22 is passed through a condenser 23 and a condensed portion of the overhead is passed as reflux to the fractionation portion 12 through line 24. The volatile liquid employed as the stripping gas may be recycled to the reaction portion 11 after recovery of the carbonyl and alcohol reaction products.

A reaction product comprised of phenol in reaction solvent and further including the liquid catalyst and some carbonyl and alcohol co-products is withdrawn from the reaction portion 11 through line 26 and, if desired, a portion thereof may be recycled to reaction portion 11 through line 27 to increase overall conversions. The remainder of the reaction product is then passed through heat exchanger 17 to effect heating of perioxide feed, as hereinabove described. The reaction product is then passed to a separation and recovery zone to recover the phenol by any one of a wide variety of recovery processes.

It is to be understood that the hereinabove procedure described with reference to the drawing is only illustrative of one processing procedure which may be employed for decomposing aromatic perioxides to a phenol in accordance with the teachings of the invention. Thus, the decomposition may be effected in a batch reaction rather than as a continuous reaction as described provided the volatile reaction products are continuously separated from the reaction mixture.

The invention will be further described with reference to the following Examples, but it is to be understood that the scope of the invention is not to be limited thereby.

EXAMPLE I 0.4542 grams of t-butyl-α-phenethyl peroxide and 14.2 mg. of p-toluene sulfonic acid dissolved in 2 ml. of ethylbenzene were placed in a flask and heated at a temperature of 70°–75° C. for a period of 15 minutes, without any means to remove the volatile reaction products. No phenol was produced.

The above procedure was repeated except that 750 cc/min of dry nitrogen were bubbled through the system and the mixture heated for a period of 20 minutes.

The yield of phenol was 77% based on consumed peroxide and the conversion was 100%. Acetaldehyde and t-butanol were also produced.

EXAMPLE II 0.4658 grams of t-butyl-α-phenethyl peroxide and 18.2 mg. of p-toluene sulfonic acid dissolved in 2 ml. of ethylbenzene were placed in a flask and heated at a temperature of 70°–75° C. for a period of 40 minutes, without any means to remove the volatile reaction products. No phenol was produced.

The above procedure was repeated, except that 750 cc/min of dry nitrogen were bubbled through the system and the mixture heated for a period of 15 minutes.

The yield of phenol was 84 % based on consumed perioxide and the conversion was 62%. Acetaldehyde and t-butanol were also produced.

EXAMPLE III 0.1184 grams of t-butyl-α-phenethyl peroxide and 25 ml. of 50% sulfuric acid dissolved in 25 ml. of ethanol were placed in a flask and heated at a temperature of 85° C. for a period of 4 minutes, while bubbling nitrogen through the system.

The yield of phenol was 79% based on consumed peroxide. Acetaldehyde and t-butanol were also produced.

EXAMPLE IV 0.1165 grams of t-butyl-α-phenethyl peroxide, 25 ml. of 50% $HClO_4$ and 25 ml. of ethanol were placed in a flask and heated at a temperature of 85° C. for a period of 5 minutes, while bubbling nitrogen through the system.

The yield of phenol was 57% based on consumed peroxide. Acetaldehyde and t-butanol were also produced.

EXAMPLE V 0.2070 grams of t-butyl-α-phenethyl peroxide dissolved in 1 ml. of ethylbenzene was placed in a flask and heated at a temperature of 68° C. for a period of 20 minutes. Gaseous sulfur dioxide was bubbled into the system, the sulfur dioxide being both the catalyst and stripping gas.

The yield of phenol was 88% based on consumed peroxide. Acetaldehyde and t-butanol were also produced.

EXAMPLE VI

A solution of di-α-phenethyl peroxide in ethylbenzene is placed in a flask and maintained at 85°–90° C. for 15 minutes while passing gaseous wet sulfur dioxide through the solution to remove volatile reaction products.

Phenol is recovered as reaction product. Acetaldehyde is also produced.

EXAMPLE VII

A solution of dicumyl peroxide and p-toluene sulfonic acid in ethylbenzene is placed in a flask and maintained at 85°–90° C. for 15 minutes while bubbling wet gaseous nitrogen through the solution to remove volatile reaction products.

Phenol is recovered as reaction product. Acetone is also produced.

EXAMPLE VIII

A solution of t-butyl (1-β-naphthylethyl) peroxide and p-toluene sulfonic acid in ethyl benzene is placed in a flask and maintained at 85°–90° C. while bubbling wet gaseous nitrogen through the solution to remove volatile products.

β-naphthol is recovered as reaction product. Acetaldehyde and t-butanol are also produced.

EXAMPLE IX

A solution of t-butyl-α-tolyl peroxide and perchloric acid in acetonitrile is placed in a flask and maintained at 85°–90° C. while bubbling steam through the solution to remove volatile components.

Phenol is recovered as reaction product. Formaldehyde and t-butanol are also produced.

EXAMPLE X 0.3966 g t-butyl-α-phenethyl peroxide and 10 mg. p-toluene sulfonic acid were dissolved in 1.8 ml ethylbenzene and 0.2 ml t-butanol in a flask and heated at a temperature of 80° C. for one hour with constant stripping by nitrogen saturated with water vapor.

The yield of phenol was 90% based on the peroxide consumed and the conversion was 89%. Acetaldehyde and t-butanol were also produced.

EXAMPLE XI

A solution of t-butyl-2-phenylisobutyl peroxide and p-toluene sulfonic acid in isobutyl benzene is placed in a flask and maintained at 85°–90° C. while bubbling wet gaseous nitrogen through the solution to remove volatile products.

Phenol is recovered as reaction product. Methyl ethyl ketone and t-butanol are also produced.

In accordance with another aspect of the invention, phenol is produced from an alkyl substituted benzene by reaction of the alkyl benzene with a t-alkyl hydroperoxide to produce the t-alkyl-α-phenalkyl peroxide which is then decomposed to phenol as hereinabove described.

More particularly, an alkyl substituted benzene, generally toluene, cumene, isobutyl benzene or ethyl benzene, is catalytically reacted with a t-alkyl hydroperoxide, preferably t-butyl hydroperoxide, at a temperature which ranges from about 70°, to about 160°, preferably from about 85° C. to about 140° C., to produce a t-butyl-α-phenalkyl peroxide. The reaction should be effected with a mole ratio of alkyl benzene to hydroperoxide of at least about 3:1 in that lower mole ratios do not provide suitable yields. In general, the mole ratio of alkyl benzene to hydropeeroxide falls within the range from about 3:1 to about 7:1, with mole ratios above about 7:1 being operable, but generally not having any additional beneficial effect upon the yield of final product.

The catalyst which is employed is generally a salt of cobalt, copper, manganese, iron or nickel, preferably a salt of copper, cobalt, iron or manganese, with cobalt and copper chloride and the naphthenates and acetylacetonates of copper and cobalt, in particular cobalt naphthenate, giving good results. The catalyst is generally employed in an amount which ranges from about 0.001 to about 0.1 mole of catalyst per mole of hydroperoxide.

The reaction may be effected with or without a diluent, and if a diluent is employed, the diluent is preferably the alcohol reaction product (t-butanol) or the corresponding alkane (isobutane).

The resulting reaction mixture, which includes peroxide, is then preferably treated to remove the catalyst, although such catalyst removal is not necessary. Thus, for example, copper naphthenate may be separated from the reaction mixture by distillation, evaporation, washing with aqueous ammonia or by washing with a dilute aqueous acid, such as sulfuric acid, at a temperature below 30° C. such that the pH of the resulting wash solution is greater than about 6, reacting the salt with sodium carbonate, filtering off the insoluble carbonate and regenerating the catalyst by reacting the carbonate with naphthenic acid. The reaction effluent, in addition to the peroxide, contains excess alkyl benzene, alcohol reaction product (t-butanol) and water, and is therefore suitable as a reaction feed for the peroxide decomposition.

The invention is further illustrated by the following Examples directed to the production of peroxides.

EXAMPLE XII

Toluene (2 moles), t-butyl hydroperoxide (0.5 mole) and cuprous chloride (0.2 gram) are premixed and heated to 70° C. The mixture is stirred in an open tank for 24 hours.

The reaction product contains t-butyl-α-tolyl peroxide.

EXAMPLE XIII

Ethyl benzene (2 moles), t-butyl hydroperoxide (0.5 mole) and cuprous chloride (0.2 gram) are premixed and heated to 70° C. The mixture is stirred in an open tank for 16 hours.

The reaction product includes t-butyl-α-phenethyl peroxide.

EXAMPLE XIV

Ethyl benzene (0.7 mole), t-butyl hydroperoxide (0.16 mole) and copper naphthenate (0.7 gram) are premixed and heated at 85° C. for 3 hours.

The product includes t-butyl-α-phenethyl peroxide.

EXAMPLE XV

Cumene (85 grams), t-butyl hydroperoxide (14 grams) and copper naphthenate (0.7 gram) are premixed and heated at 75° C.

The reaction product includes t-butyl-cumyl peroxide.

EXAMPLE XVI

Ethylbenzene (0.71 mole), t-butyl hydroperoxide (0.157 mole) and copper naphthenate (0.743 gram) were premixed and brought up to 85° C. Heating was continued for 3 hours under reflux conditions at atmospheric pressure.

The reaction product contained t-butyl-α-phenethyl peroxide and t-butanol.

EXAMPLE XVII

Isobutyl benzene (0.7 mole), t-butyl hydroperoxide (0.16 mole) and copper naphthenate (0.7 gram) are premixed and heated to 85° C. Heating is continued for 3 hours under reflux conditions at atmospheric pressure.

The reaction product contains t-butyl-2-phenylisobutyl peroxide.

The process of the invention has numerous advantages with the primary advantage being the ability to effectively produce phenol from an alkyl benzene through a relatively stable intermediate. Thus, current processes which produce phenol through the cumene route use cumyl hydroperoxide as an intermediate, an intermediate which is generally unstable. In addition, the present overall process permits the production of carbonyl byproducts other than acetone; e.g., t-butanol and acetaldehyde or formaldehyde, thereby providing more marketing flexibility.

Numerous modification and variations of the present invention are possible in light of the above teachings and therefore, within the scope of the appended claims the invention may be practiced other than as particularly described.

What is claimed is:

1. A process for producing a phenol comprising: catalytically reacting by heating in the liquid phase an alkyl benzene selected from the group consisting of toluene, cumene isobutyl benzene and ethyl benzene with t-butyl hydroperoxide in the presence of a catalyst selected from the group consisting of the chlorides, naphthenates and acetylacetonates of cobalt, copper, manganese, iron and nickel to produce the corresponding t-butyl-α-phenalkyl peroxide; heating a reaction mixture comprising the t-butyl-α-phenalkyl peroxide and an acid catalyst to decompose the peroxide; said heating being effected to provide a temperature at which the carbonyl and alkanol decomposition products of said peroxide can be separated from the reaction mixture in gaseous form and the phenol decomposition product of said peroxide is a liquid; continuously separating from the reaction mixture, in gaseous form, the carbonyl and alkanol decomposition products; and recovering the phenol from the reaction mixture.

2. The process as defined in claim 1 wherein the reaction mixture is maintained at a temperature from about 20° C. to about 150° C.

3. The process as defined in claim 2 wherein the volatile carbonyl and alkanol reaction products are continuously separated from the reaction mixture by bubbling a stripping gas through the reaction mixture.

4. The process as defined in claim 2 wherein the reaction mixture is passed downwardly through a vertical reactor and the other reaction products are removed from the top of the reactor.

5. The process as defined in claim 1 wherein the mole ratio of alkyl benzene to hydroperoxide ranges from about 3:1 to about 7:1.

6. The process as defined in claim 5 wherein the alkyl benzene is reacted with the hydroperoxide at a temperature ranging from about 70° to about 160° C.

7. The process of claim 2 wherein the reaction mixture includes water.

* * * * *